United States Patent [19]

Dionne et al.

[11] 4,319,029

[45] Mar. 9, 1982

[54] HYDROXYALKANAMIDE TETRAHYDROCARBAZOLES

[75] Inventors: Gervais Dionne; Andre A. Asselin, both of St. Laurent; Leslie G. Humber, Dollard des Ormeaux, all of Canada

[73] Assignee: American Home Products Corporation, New York, N.Y.

[21] Appl. No.: 157,734

[22] Filed: Jun. 9, 1980

Related U.S. Application Data

[62] Division of Ser. No. 64,343, Aug. 6, 1979, Pat. No. 4,235,903.

[51] Int. Cl.³ .................. C07D 413/06; C07D 209/86
[52] U.S. Cl. .................... 544/142; 546/200; 260/315; 260/326.25; 260/326.27
[58] Field of Search .................. 544/142; 546/200; 260/315, 326.25, 326.27

[56] References Cited

U.S. PATENT DOCUMENTS

| | | | |
|---|---|---|---|
| 3,843,681 | 10/1974 | Demerson et al. | 260/326.14 |
| 3,859,304 | 1/1975 | Dostert et al. | 260/315 |
| 3,880,853 | 4/1975 | Demerson et al. | 424/267 |
| 4,128,560 | 12/1978 | Asselin et al. | 260/315 |

OTHER PUBLICATIONS

Dostert et al., *Chem. Abstracts,* vol. 84 (1976), No. P30889y.

*Primary Examiner*—Henry R. Jiles
*Assistant Examiner*—R. W. Ramsuer
*Attorney, Agent, or Firm*—Arthur E. Wilfond

[57] ABSTRACT

Indole derivatives characterized by having a 1,2,3,4-tetrahydrocarbazole or 1,2,3,4-tetrahydrocyclopent[b]indole nucleus with a hydroxyalkanamine substituent are disclosed. The nucleus is optionally further substituted at various positions. The derivatives are useful diuretic agents, and methods for the preparation and use are also disclosed.

1 Claim, No Drawings

HYDROXYALKANAMIDE TETRAHYDROCARBAZOLES

This is a division of application Ser. No. 64,343, filed Aug. 6, 1979, now U.S. Pat. No. 4,235,903.

BACKGROUND OF THE INVENTION (a) Field of the Invention

This invention relates to novel tetrahydrocarbazole derivatives, to a process and to intermediates for preparing the derivatives, to methods for using the derivatives and to compositions and therapeutically acceptable salts of the derivatives.

More specifically, the present invention relates to novel 1,2,3,4-tetrahydrocarbazole and 1,2,3,4-tetrahydrocyclopent[b]indole derivatives having a hydroxyalkanamine group. These derivatives are useful as diuretic agents in a mammal at dosages which do not elicit undesirable side effects. The combination of these attributes render the 1-hydroxyalkanamine tetrahydocarbazole derivatives of this invention therapeutically useful.

The 1-hydroxyalkanamine tetrahydrocarbazole derivatives of this invention belong to a special class of diuretic agents which antagonize the renal effects of mineralocorticoids. As a result, these compounds are useful in treating hyperaldosteronism by increasing urine volume and sodium and chloride excretion without affecting potassium excretion. Also, these compounds find utility in the treatment of edema and hypertension.

(b) Description of the Prior Art

A number of reports dealing with tetrahydrocarbazole derivatives are available. For instance, a number of these derivatives are reported are reported by C. A. Demerson et al., in U.S. Pat. No. 3,843,681, issued Oct. 22, 1974; C. A. Demerson et al., in U.S. Pat. No. 3,880,853, issued Apr. 29, 1975; Dostert et al., U.S. Pat. No. 3,859,304, issued Jan. 7, 1975 and A. A. Asselin et al., U.S. Pat. No. 4,128,560, issued Dec. 5, 1978.

The compounds of the present invention are distinguished from the compounds of the above prior art by the nature of the substituents on the tetrahydrocarbazole nucleus and by their pharmacologic properties. More specifically, the novel compounds of this invention are distinguished from the prior art compounds by having a hyroxyalkanamine group. In addition, the novel 1-hydroxyalkanamine tetracarbazole derivatives of this invention possess useful diuretic activity in mammals, a pharmacologic activity not previously reported for tetracarbazole derivatives.

Asselin et al., application Ser. No. 904,081, filed May 8, 1978 now U.S. Pat. No. 4,179,503, shows 1,3,4,9-tetrahydropyrano[3,4-b]indole and 1,3,4,9-tetrahydrothiopyrano[3,4-b]-indole derivatives having a hydroxyalkanamine and a lower alkyl group at position 1. The compounds of the present invention are distinguished therefrom in having a different ring structure.

SUMMARY OF THE INVENTION

The compounds of this invention are represented by formula I

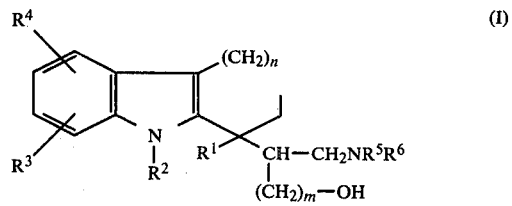

in which $R^1$ and $R^2$ each is hydrogen or lower alkyl; $R^3$ and $R^4$ each is hydrogen, lower alkyl, halo, nitro, trifluoromethyl or lower alkoxy; $R^5$ and $R^6$ each is hydrogen or lower alkyl or $R^5$ and $R^6$ together with the nitrogen atom to which they are attached form a pyrrol-1-yl, piperidin-1-yl or morpholin-4-yl; m is 2 or 3; and n is 1 or 2; or a therapeutically acceptable acid addition salt thereof.

A preferred group of compounds of this invention is represented by formula I in which $R^1$ and $R^2$ each is hydrogen or lower alkyl; $R^3$ and $R^4$ each is hydrogen, lower alkyl or halo; $R^5$ and $R^6$ each is hydrogen or lower alkyl; m is 2 or 3; and n is 1 or 2.

A more preferred group of compounds of this invention is represented by formula I in which $R^1$ is hydrogen or lower alkyl; $R^2$, $R^3$ and $R^4$ are hydrogen; $R^5$ and $R^6$ each is hydrogen or lower alkyl; m is 2 or 3; and n is 2.

A most preferred group of compounds of this invention is represented by formula I in which $R^1$, $R^5$ and $R^6$ each is lower alkyl; $R^2$, $R^3$ and $R^4$ are hydrogen; and m and n are 2.

A compound of formula I or a therapeutically acceptable acid addition salt thereof increases the excretion of urine (diuresis) in a mammal, antagonizes renal mineralocorticoids in a mammal, increases the excretion of urine in a mammal without excessive loss of potassium, reverses or prevents secondary aldosteronism and potassium depletion induced in a mammal undergoing diuretic therapy, and is useful for treating hypertension.

A pharmaceutical composition is provided by combining a compound of formula I, or a therapeutically acceptable salt thereof, with a pharmaceutically acceptable carrier.

In addition, a compound of formula I, or a therapeutically acceptable salt thereof, in combination with a non-mineralocorticoid antagonizing diuretic agent and a pharmaceutically acceptable carrier forms a pharmaceutical composition.

The compounds of formula I in which $R^1$, $R^2$, $R^3$, $R^4$, $R^5$, $R^6$, m and n are as defined herein are prepared by a process, which comprises reacting a compound of formula II in which $R^1$, $R^2$, $R^3$, $R^4$, m and n

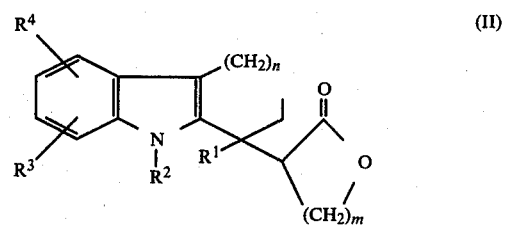

are as defined herein with an amine of formula $HNR^5R^6$ in which $R^5$ and $R^6$ are as defined herein to obtain the corresponding compound of formula III

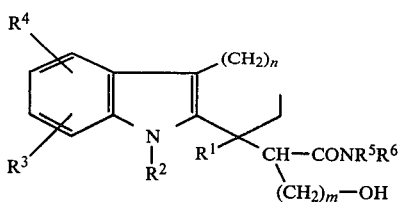

(III)

in which $R^1$, $R^2$, $R^3$, $R^4$, $R^5$, $R^6$, m and n are as defined herein, and reducing the compound of formula III with a complex metal hydride.

DETAILED DESCRIPTION OF THE INVENTION

The term "lower alkyl" as used herein means straight chain alkyl radicals containing from one to six carbon atoms and branched chain alkyl radicals containing from three to four carbon atoms and includes methyl, ethyl, propyl, isopropyl, butyl, isobutyl, pentyl, hexyl and the like.

The term "lower alkoxy" as used herein means straight chain alkoxy radicals containing from one to six carbon atoms and branched chain alkoxy radicals containing three or four carbon atoms and includes methoxy, ethoxy, isopropoxy, butoxy, hexanoxy and the like.

The term "halo" as used herein means halogens and includes fluorine, chlorine, bromine and iodine, unless stated otherwise.

The term "complex metal hydride" as used herein means the metal hydrides, including lithium aluminum hydride, lithium aluminum hydride-aluminum chloride, aluminum hydride-aluminum chloride, borane, borane-methyl sulfide, sodium borohydride-aluminum chloride, diisobutylaluminum hydride and the like.

The compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding bases. For many purposes it is preferable to administer the salts rather than the base compounds. Suitable acids to form these salts include the common mineral acids, e.g. hydrohalic, sulfuric or phosphoric acid, the organic acids, e.g. maleic, citric, or tartaric acid, and acids which are sparingly soluble in body fluids and which impart slow-release properties to their respective salts, e.g. pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

Also included in this invention are the stereochemical isomers of the compounds of formula I which result from asymmetric centers contained therein. Such stereochemical isomers are obtained in substantially pure form by classical separation techniques and by sterically controlled synthesis and have arbitrarily been named as isomers A and B, respectively.

Individual optical enantiomers, which might be separated by fractional crystallization of the diastereomeric salts thereof, for instance, salts with d- or l-tartaric acid or D-(+)-α-bromocamphor sulfonic acid, are also included.

The compounds of this invention of formula I or a therapeutically acceptable salt thereof are useful diuretic agents in a mammal upon oral or parenteral administration.

The compounds of formula I are shown to be effective diuretic agents in mammals by tests conducted in dogs or rats. An example of such a test for diuretic agents in rats is described by J. R. Cummings et al., J. Pharmacol. Exp. Ther., 414, 128 (1960). In this test, the urine of the rats is collected for five hours, during which time food and water are withdrawn. Urine volumes as well as sodium, potassium and chloride ion concentrations are determined. In this test, the compounds of this invention exhibit a dose-response dependency when they are orally administered in dosages ranging from 50 to 300 mg per kilogram of body weight. For example, the following representative compounds of formula I are effective diuretic agents when administered to the rat (the effective oral dose in mg per kilogram of body weight to obtain a three fold increase in urine volume and/or electrolyte concentration is indicated within the parentheses): isomer A of γ-[(dimethylamino)methyl]-1-methyl-1,2,3,4-tetrahydrocarbazole-1-propanol (100 mg, described in Example 1) and isomer B of γ-[(dimethylamino)methyl]-1-methyl-1,2,3,4-tetrahydrocarbazole-1-propanol (100 mg, described in Example 1).

In addition to the above test for diuretic activity, the compounds of formula I antagonize the renal actions of mineralocorticoids and thus cause an increase in sodium and chloride excretion without affecting potassium excretion.

Aldosterone is a naturally occurring mineralocorticoid of the adrenal cortex which promotes the reabsorption of sodium and chloride and the excretion of potassium, hydrogen and ammonium ions in the distal renal tubules. Hyperaldosteronism is found in a number of pathological conditions. Hyperladosteronism can be corrected by the administration of a diuretic agent which antagonizes the renal action of aldosterone.

Antialdosterone activity can be demonstrated in standard test systems. One such test is described by C. M. Kagawa et al., J. Pharm. Exp. Ther., 126, 123 (1959). In this test albino rats (140–160 g) are kept under laboratory conditions for four days, after which they are bilaterally adrenalectomized under diethyl ether anesthesia. The animals are then maintained for 48 hours on a diet of Purina Rat Chow and 5% (W/V) glucose solution (ad libitum). Prior to the test the animals are starved for eighteen hours, but are allowed access to the 5% (W/V) glucose solution. Each rat then receives a single subcutaneous injection of physiological saline (2.5 ml) followed by a subcutaneous injection of desoxycorticosterone acetate (DOCA, 12.5 mcg per rat). The test compound is administered orally. The rats are placed in metabolism cages and the urine is collected for four hours. Urine volume and urinary sodium, potassium and chloride are measured. In this test the compounds of this invention are effective by showing a dose response dependency in the range of 3 to 100 mg/kg of body weight. More specifically, this test shows that the following representative compounds of formula I are effective diuretic agents by increasing the urine volume and sodium and chloride excretion when administered to the rat (the effective oral dose in mg per kilogram of body weight to obtain a statistically significant increase in urine volume and sodium and chloride concentration is indicated in the parenthesis): isomer A of γ-[(dimethylamino)methyl]-1-methyl-1,2,3,4-tetrahydrocarbazole-1-propanol (6.25 mg, described in Example 1) and isomer B of γ-[(dimethylamino)methyl]-1-methyl-1,2,3,4-tetrahydrocarbazole-1-propanol (50 mg, described in Example 1).

Another test for antialdosterone diuretic activity, described by C. M. Kagawa et al., Arch. Pharmacodyn. Ther., 149, 8 (1964) can be conducted in intact female dogs. The dogs are given 0.25 mg of DOCA in 0.25 ml of sesame oil intramuscularly and the test drug orally by capsule two hours before the beginning of infusion. A retention catheter is placed in the bladder for urine collection, and the cephalic vein is cannulated for infusion. Saline, 0.45%, plus dextrose, 5%, is unfused intravenously at a rate of 1 ml/kg/min for 20 minutes, after which the rate is reduced to 0.3 ml/kg/min for the duration of the experiment. Urine is collected at 30 minute intervals, the urine volumes are recorded, and samples are taken. Collections are continued for five 30 minute periods. The urine samples are analyzed and the urinary Na/K ratios are calculated. By using this test, the compounds of formula I can be shown to be effective diuretic agents by increasing urine volume and sodium and chloride excretion when administered to the dog.

The compounds of formula I can be administered to a mammal in a combination with a therapeutically effective dose of a diuretic agent, acting by another mechanism. These latter diuretics, non-renal mineralocorticoid antagonizing diuretics, cause loss of water as well as the electrolytes sodium, potassium, etc. Suitable diuretics for this combination, together with their daily dosage, are set out below:

| Diuretic | Recommended daily human dosage range (mg/70 Kg) |
|---|---|
| hydrochlorothiazide | 25–100 |
| chlorothiazide | 500–1000 |
| chlorthalidone | 50–200 |
| ethacrynic acid | 50–200 |
| furosemide | 40–80 |
| quinethazone | 50–100 |
| bumetanide | 1–2 |

The following method illustrates that the combination of the compound of formula I with a diuretic agent can result in a useful reduction of potassium excretion.

Male albino Sprague-Dawley rats weighing 180 to 200 g are divided into four groups of seven rats each. At the beginning of the test the bladder of each rat is emptied by gentle suprapubic pressure. The required dose of the compound of formula I and/or diuretic agent is suspended in 2% (W/V) starch solution and administered orally. The control group receives the vehicle only. Each rat receives 5 ml of 0.9% sodium chloride per 100.0 gram of body weight orally. The rats are placed in individual metabolism cages and urine is collected for five hours after which the bladder is again emptied by gentle suprapubic pressure. All urine samples are analyzed for Na, K and Cl content and Na/K ratios are calculated.

The combination of a compound of formula I with other diuretic agents is useful for treating certain disease states, for instance, secondary hyperaldosteronism, as a result of pathologic conditions such as ascites due to cirrhosis of the liver. In addition, the use of a compound of formula I, given sequentially or simultaneously, in combination with another diuretic agent can allow the reduction of the usual therapeutic dose of the other diuretic and still cause sufficient sodium excretion without excessive potassium loss.

The above described test methods for diuretic activity illustrate that the diuretic effect of the compounds of formula I is primarily due to the antagonism of mineralocorticoids on renal electrolyte excretion and in part results from an additional direct renal tubular effect. From the above test methods, the compounds of formula I exhibit a separation of diuretic and anti-aldosterone diuretic activities by possessing effective antialdosterone diuretic activity at lower doses than required for effective diuretic activity. Furthermore, the compounds of formula I, when tested as described above, are non-toxic when administered in effective diuretic and antialdosterone diuretic amounts. In addition, since the compounds of formula I are non-steroidal, the compounds of formula I do not exhibit the undesirable side effects of steroidal antagonists of mineralocorticoids. Such common side effects of steroidal antagonists are gynecomastia, impotence and irregular menses.

In addition to their use as diuretic agents, the compounds of formula I or a therpaeutically acceptable acid addition salt thereof are useful agents for the treatment of hypertension in a mammal. For the treatment of hypertension in a mammal, the compounds of formula I are administered in the same manner as described herein for their use as diuretic agents. When used for the treatment of hypertension, the compound of formula I can be administered alone or administered sequentially or simultaneously in combination with an effective amount of a non-mineralocorticoid antagonizing diuretic agent. Furthermore, a combination of an antihypertensive effective amount of an antihypertensive agent with the compound of formula I, or a therapeutically acceptable acid addition salt thereof; or a combination of an antihypertensive effective amount of an antihypertensive agent with the compound of formula I, or a therapeutically acceptable acid addition salt thereof, and an effective amount of a non-mineralocorticoid antagonizing diuretic agent is useful for the treatment of hypertension in a mammal. Suitable antihypertensive agents for use in this combination can be selected from Rauwolfia and related alkaloids e.g. reserpine, syrosingopine, deserpidine, rescinnamine; guanethidines, e.g. guanethidine, 2-heptamethylineimino-ethylguanidine or related guanidines covered in U.S. Pat. No. 2,928,829 by R. P. Mull, issued Mar. 15, 1960, herein incorporated by reference; veratrum alkaloids, e.g. protoveratrines A and B or germine; hydralazine; diazoxide; minoxidil; nitroprusside, phentolamine; phenoxybenzamine; pargyline; chlorisondamine, hexamethonium, mecamylamine, pentoliniuim; trimethaphan; clonidine; methyldopa; and propranolol. A combination of antihypertensive agents, for example reserpine and hydralazine, can be substituted for a single antihypertensive agent, as described above. Suitable methods of adminstration, compositions and dosages of the above described antihypertensive agents are described in medical textbooks, for instance, see Charles E. Baker, Jr. "Physician's desk reference", Medical Economics Company, Oradell, N.J., 1977. For example, the antihypertensive agent propranolol is administered orally as propranolol hydrochloride (IND- ERAL, "Inderal" is a trade mark) to humans in the effective dose range of 80 to 640 mg per day. The compounds of formula I, when administered in combination with an antihypertensive agent or an anti-hypertensive agent plus a non-mineralocorticoid antagonizing diuretic agent for the treatment of hypertension, are used in the same manner as described herein for their use as diuretic agents.

When the compounds of formula I of this invention are used as diuretic and/or antialdosterone agents in mammals, e.g. rats and dogs, they are used alone or in combination with pharmacologically acceptable carriers, the proportion of which is determined by the solubility and chemical nature of the compound, chosen route of administration and standard biological practice. For example, they are administered orally in solid form i.e. capsule or tablet. They are also administered orally in the form of suspensions or solutions or be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of the invention contain the active ingredient in admixture with one or more non-toxic pharmaceutical excipients known to be suitable in the manufacture of aqueous suspensions. Suitable excipients are, for example, methyl-cellulose, sodium alginate, gum acacia, lecithin and so forth. The aqueous suspension can also contain one or more preservatives, one or more colouring agents and/or one or more sweetening agents.

Non-aqueous suspensions can be formulated by suspending the active ingredient in a vegetable oil, for example, arachis oil, olive oil, sesame oil, or coconut oil; or in a mineral oil. The suspension can contain a thickening agent, for example beeswax, hard paraffin or cetyl alcohol. These compositions can also contain a sweetening agent, flavouring agent and antioxidant.

The dosage of the compounds of formula I of this invention as diuretic and antialdosterone agents will vary with the form of administration and the particular host as well as the age and condition of the host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. The effective diuretic and antialdosterone amount of the compounds usually ranges from about 0.5 mg to about 500 mg per kilogram of body weight per day, although as aforementioned variations will occur. However a dosage level that is in the range of from about 2 mg to about 300 mg per kilogram of body weight per day is employed most desirably in order to achieve effective results.

PROCESS

The process for the preparation of the compounds of formula I is illustrated in reaction scheme 1.

REACTION SCHEME 1

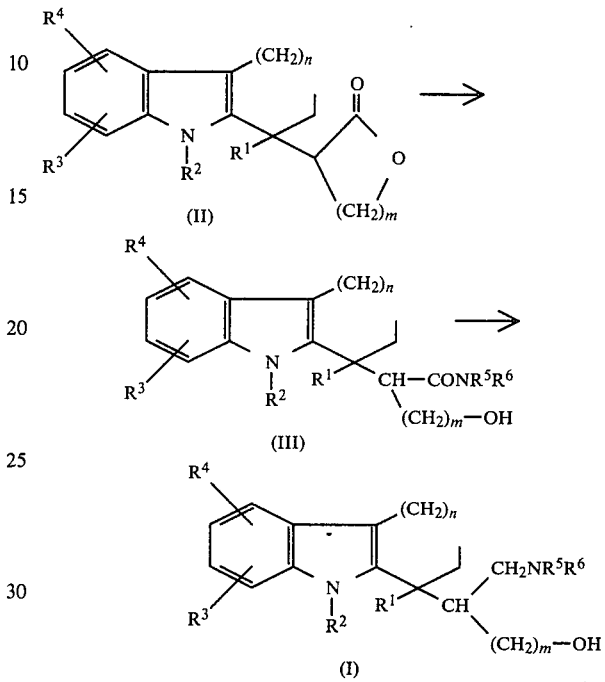

With reference to reaction scheme 1, a compound of formula II in which $R^1$, $R^2$, $R^3$, $R^4$, m and n are as defined herein is reacted with 20 to 40 molar equivalents of an amine of formula $HNR^5R^6$ in which $R^5$ and $R^6$ are as defined herein in an inert organic solvent, preferably methanol, tetrahydrofuran or dioxane, at 50° to 80° C. for two to ten days to obtain the corresponding amide of formula III in which $R^1$, $R^2$, $R^3$, $R^4$, $R^5$, $R^6$, m and n are as defined herein.

The amide of formula III is reduced with a complex metal hydride to obtain the corresponding compound of formula I in which $R^1$, $R^2$, $R^3$, $R^4$, $R^5$, $R^6$, m and n are as defined herein. Examples of suitable complex metal hydrides are lithium aluminum hydride, lithium aluminum hydride-aluminum chloride, aluminum hydride-aluminum chloride, diborane, diisobutylaluminum hydride, borane-methyl sulfide and sodium borohydride-aluminum chloride. Lithium aluminum hydride or diisobutylaluminum hydride is preferred. Preferred inert solvents for use with the complex metal hydrides are the nonhydroxylic solvents, for example, diethyl ether, dioxane, tetrahydrofuran, 1,2-dimethoxyethane and the like. The choice of solvent will depend on solubility of reactants and temperature required for reduction. Usually the reduction is conducted at 0° to 100° C., preferably 30° to 70° C., for one to ten hours. The preferred amount of complex metal hydride in the range of two to ten molar equivalents.

A method of preparing the compounds of formula II is illustrated in reaction scheme 2.

REACTION SCHEME 2

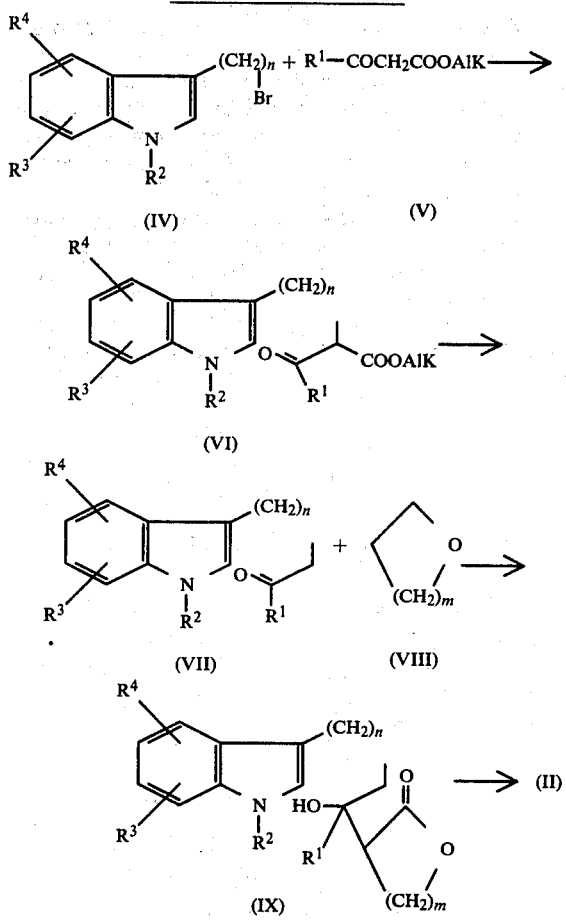

ing compound of formula IX in which $R^1$, $R^2$, $R^3$, $R^4$, m and n are as defined herein.

Cyclization of the compound of formula IX with 5 to 20 molar equivalents of boron trifluoride etherate at 100° to 130° C. for 30 minutes to two hours gives the corresponding compound of formula II in which $R^1$, $R^2$, $R^3$, $R^4$, m and n are as defined herein.

The above described series of reactions as illustrated in reaction scheme 2 is especially useful for preparing the compounds of formula II in which $R^1$, $R^2$, $R^3$ and $R^4$ are as defined herein, and m and n are 2.

Another method of preparing the compounds of formula II is illustrated in reaction scheme 3, wherein a keto-ester of formula X in which $R^1$ and n are as defined herein and Alk is lower alkyl is reacted with about one molar equivalent of trimethylorthoformate in the presence of a catalytic amount of concentrated sulfuric acid in anhydrous methanol at 60° to 70° C. for two to seven hours to obtain the corresponding compound of formula XI in which $R^1$, n and Alk are as defined herein.

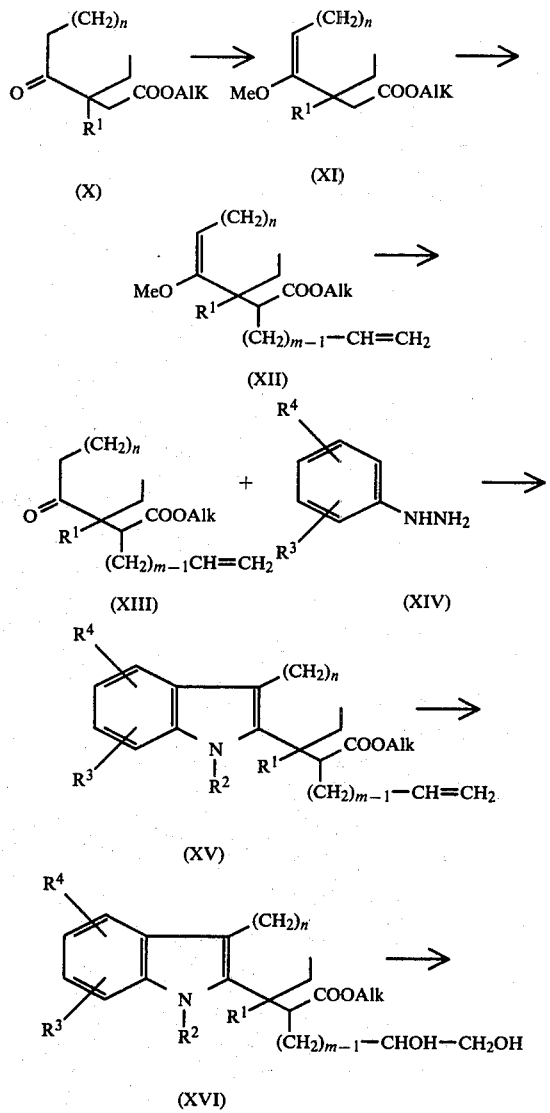

As illustrated in reaction scheme 2, an indole derivative of formula IV in which $R^2$, $R^3$, $R^4$ and n are as defind herein is condensed with about one molar equivalent of a keto-ester of formula V in which $R^1$ is as defined herein and Alk is lower alkyl in the presence of about one molar equivalent of sodium hydride in tetrahydrofuran at about 40° to 70° C. for 10 to 40 hours to obtain the corresponding compound of formula VI in which $R^1$, $R^2$, $R^3$, $R^4$, n and Alk are as defined herein.

Decarboxylation of the compound of formula VI with about 1.5 to 2.0 molar equivalents of barium hydroxide in aqueous ethanol at 60° to 90° C. for 10 to 30 hours followed by acidification of the reaction mixture with dilute hydrochloric acid gives the corresponding compound of formula VII in which $R^1$, $R^2$, $R^3$, $R^4$ and n are as defined herein.

In the next step, the anion of the lactone of formula VIII in which m is as defined herein is first prepared by reacting diisopropylamine with about one molar equivalent of butyllithium in anhydrous tetrahydrofuran at about 0° to 5° C. for 10 to 20 minutes and about one molar equivalent of the lactone of formula VIII is added, the resulting solution is stirred at −50° to −78° C. for 10 to 20 minutes to give a solution containing the anion of the lactone of formula VIII. To this solution is added a solution of about one-half molar equivalent of the compound of formula VII in a solvent consisting of hexamethylphosphoric triamide and tetrahydrofuran, and the resulting solution is maintained at about −30° to −50° C. for 30 to 60 minutes to obtain the correspond- -continued
REACTION SCHEME 3

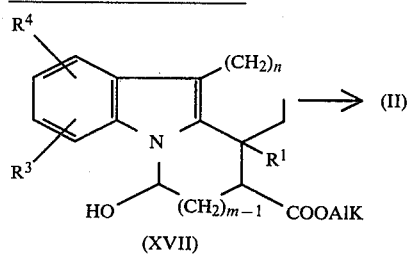

(XVII)

Alkylation of the compound of formula XI affords the corresponding compound of formula XII in which $R^1$, m, n and Alk are as defined herein. This alkylation is readily achieved by the following steps: a solution of diisopropylamine and about one molar equivalent of butyllithium in a mixture of tetrahydrofuran and hexane is stirred at 0° to 5° C. for about 15 minutes and cooled to −50° to −78° C.; about one molar equivalent of the compound of formula XI is added and the resulting mixture is stirred at −50° to −78° C. for 30 minutes to two hours; a solution of about one molar equivalent of 3-bromo-1-propene or 4-bromo-1-butene in a solvent of hexamethylphosphoric triamide is added and the resulting solution is stirred at about −50° to −78° C. for 30 minutes to two hours and at 20° to 30° C. for 20 to 30 hours; and the compound of formula XII is isolated.

Hydrolysis of the compound of formula XIi with 0.01 to 0.1 molar equivalents of concentrated hydrochloric acid in aqueous methanol at 60° to 70° C. for 30 minutes to two hours gives the corresponding compound of formula XIII in which $R^1$, m and Alk are as defined herein.

Condensation of the compound of formula XIII with a phenyl hydrazine of formula XIV in which $R^3$ and $R^4$ are as defined herein according to the conditions of the Fischer indole reaction gives the corresponding indole of formula XV in which $R^1$, $R^2$, $R^3$, $R^4$, m, n and Alk are as defined herein. Preferred conditions for this Fischer indole reaction involves: reacting the compound of formula XIII with an equivalent molar amount of the phenyl hydrazine of formula XIV in isobutanol under anhydrous conditions at 100° to 110° C. for 20 to 30 hours; evaporating the latter solution; reacting the residue with aqueous sulfuric acid solution, preferably about ten percent sulfuric acid, at 90° to 110° C. for 10 to 20 minutes; and isolating the indole of formula XV.

The indole of formula XV is reacted with about one molar equivalent of osmium tetroxide in a solvent of tetrahydrofuran and pyridine at about −78° C. for about 10 minutes and at about 0° C. for one to three hours to obtain the diol of formula XVI in which $R^1$, $R^2$, $R^3$, $R^4$, m, n and Alk are as defined herein.

Oxidation of the compound of formula XVI in which $R^1$, $R^3$, $R^4$, m, n and Alk are as defined herein and $R^2$ is hydrogen with about one molar equivalent of sodium metaperiodate in a solution of aqueous acetone at 50° to 70° C. for 10 to 50 seconds, followed by the addition of a catalytic amount of phosphoric acid, and heating the resulting solution at 50° to 70° C. for 20 to 40 minutes gives the corresponding compound of formula XVII in which $R^1$, $R^3$, $R^4$, m, n and Alk are as defined herein. Reduction of the latter compound with about one molar equivalent of sodium borohydride in ethanol at 20° to 30° C. for 10 to 25 hours gives the corresponding compound of formula II in which $R^1$, $R^3$, $R^4$, m and n are as defined herein and $R^2$ is hydrogen.

Similarily, oxidation of the compound of formula XVI in which $R^1$, $R^3$, $R^4$, m, n and Alk are as defined herein and $R^2$ is lower alkyl with sodium metaperiodate followed by reduction of the aldehyde, so formed, with sodium borohydride gives the corresponding compound of formula II in which $R^1$, $R^3$, $R^4$, m and n are as defined herein and $R^2$ is lower alkyl.

The above described series of reactions, as illustrated in reaction scheme 3, is especially useful for preparing the compounds of formula II in which $R^1$, $R^2$, $R^3$ and $R^4$ are as defined herein, and m and n are 2.

A preferred method of preparing the compounds of formula II in which $R^1$, $R^2$, $R^3$, $R^4$ and m are as defined herein and n is 1 is illustrated in reaction scheme 4.

REACTION SCHEME 4

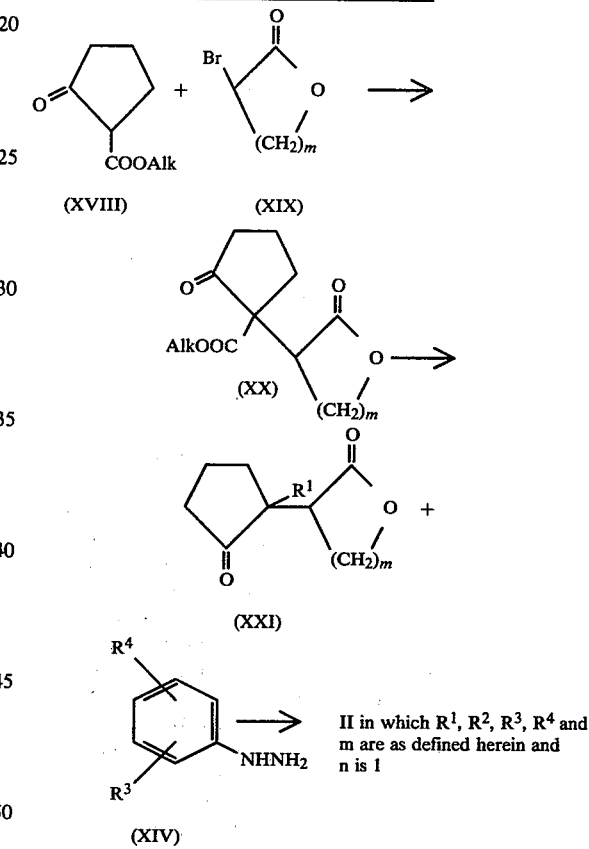

As illustrated in reaction scheme 4, an ester of formula XVIII in which Alk is lower alkyl is condensed with one to three molar equivalents of a lactone of formula XIX in which m is as defined herein in the presence of two to five molar equivalents of potassium carbonate in acetone to give the corresponding compound of formula XX in which Alk and m are as defined herein.

Hydrolysis of the compound of formula XX, preferably with a solution of 10 to 30% sulfuric acid at 80° to 100° C. for 18 to 30 hours, gives the corresponding compound of formula XXI in which $R^1$ is hydrogen and m is as defined herein.

If desired, the latter compound of formula XXI is alkylated with a lower alkyl bromide, chloride or iodide, in the same manner as described above for the alkylation of the compound of formula XI with 3-bromo-1-propene or 4-bromo-1-butene, to give the corresponding compound of formula XXI in which $R^1$ is lower alkyl and m is as defined herein.

The compound of formula XXI in which $R^1$ and m are as defined herein is condensed with a phenyl hydrazine of formula XIV in which $R^3$ and $R^4$ are as defined herein according to the conditions of the Fischer indole reaction, in the same manner as described above, to give the corresponding compound of formula II in which $R^1$, $R^2$, $R^3$, $R^4$ and m are as defined herein and n is 1.

The following examples illustrate further this invention.

EXAMPLE 1

γ-[(Dimethylamino)methyl]-1-methyl-1,2,3,4-tetrahydrocarbazole-1-propanol (I: $R^1$, $R^5$ and $R^6$=Me, $R^2$, $R^3$ and $R^4$=H, and m and n=2)

A 50% sodium hydride dispersion in oil (3.71 g, 0.077 mole) was washed with petroleum ether to remove the oil and the hydride was covered with tetrahydrofuran (50 ml) which has been freshly distilled over lithium aluminum hydride. To the stirred suspension was added dropwise, via a septum, ethyl acetoacetate (V: $R^1$=Me and Alk=Et; 9.8 ml, 0.077 mole). To this solution was added rapidly 3-(2-bromoethyl)-indole (IV: $R^2$, $R^3$ and $R^4$=H and n=2; 15.7 g, 0.070 mole). The resulting mixture was refluxed for 20 hr. After cooling, the reaction mixture was poured into water and the product was extracted with diethyl ether. The extract was washed with water and dried over magnesium sulphate. Evaporation of solvent afforded an oil (15.2 g) which was chromatographed through a column of silica gel (840 g) using 10% acetone in benzene to give 2-acetyl-4-(1H-indol-3-yl)-butanoic acid, ethyl ester (VI: $R^1$=Me, $R^2$, $R^3$ and $R^4$=H, n=2 and Alk=Et) as an oil: nmr(CDCl$_3$) δ 1.25 (t, 3H), 2.15 (s, 3H), 2.25 (m, 2H), 2.75 (m, 2H), 3.45 (t, 1H), 4.13 (q, 2H), 7.2 (m, 5H) and 7.95 (s, 1H), and Anal. Calcd for $C_{16}H_{19}NO_3$: C, 70.30% H, 7.01% N, 5.12% and Found: C, 70.00% H, 7.07% N, 4.87%.

To a mixture of barium hydroxide octahydrate (3.18 g) in water (48 ml) was added a solution of the latter keto ester (2.32 g, 0.085 moles) in ethanol (12 ml). This mixture was refluxed and stirred for 18 hr. After cooling, the solution was acidified with 6 N hydrochloric acid (effervescence) and the product was extracted with methylene chloride. The organic layer was washed with water and dried over magnesium sulphate. Evaporation of solvent afforded an oil (1.66 g) which crystallized on standing. This was chromatographd through a silica gel column (48 g) using 10% acetone in benzene to give 1.22 g of a residue which was crystallized from dichloromethane-hexane to give 3-(4-oxopentyl)-indole: mp 89°–90° C.; nmr(CDCl$_3$) δ 2.05 (s, 3H), 2.4 (m, 6H), 7.1 (m, 4H) and 7.85 (broad, 1H); and Anal. Calcd for $C_{13}H_{15}NO$: C, 77.58% H, 7.51% N, 6.96% and Found: C, 77.83% H, 7.47% N, 6.67%.

To diisopropylamine (1.68 ml, 0.012 moles) in anhydrous tetrahydrofuran (12 ml, freshly distilled over lithium aluminum hydride) at 4° C. was added dropwise through a septum, a 2.3 M solution of butyllithium in hexane (5.2 ml, 0.012 moles) maintaining the temperature at 4° C. This was stirred at this temperature for 15 min then cooled to −78° C. To this solution was added dropwise a solution of γ-butyrolactone (VIII: m=2; 0.93 ml, 0.012 moles) in dry tetrahydrofuran (12 ml). This was stirred at −78° C. for 20 min and then a solution of 3-(4-oxopentyl)-indole (1.2 g, 0.012 moles) in a mixture of dry tetrahydrofuran (3 ml) and hexamethylphosphoric triamide (2.5 ml) was added. The temperature was raised to −40° C. and maintained at this temperature for 45 min. The cooling bath was removed and water (30 ml) was added to the solution. The reaction mixture was poured into water and the product was extracted with diethyl ether. The extract was washed with water and dried over magnesium sulphate. Evaporation of solvent afforded an oil (1.72 g) which was chromatographed through a silica gel column (40 g) using 35% acetone in benzene to afford an oil (1.44 g) of the diastereoisomeric mixture of dihydro-3-[2-hydroxy-5-(1H-indol-3-yl)-2-pentyl]-2(3H)-furanone: ir(CHCl$_3$) 3470 and 1750 cm$^{-1}$; and nmr(CDCl$_3$) δ 1.17 and 1.25 (singlets, 3H), 2.5–3.0 (m, 3H), 3.9–4.4 (m, 2H), 6.9 (s, 1H), 7.0–7.6 (m, 4H) and 7.92 (broad, 1H).

A diastereoisomeric mixture of the latter hydroxy lactone (410 mg, 0.0014 mole) in boron trifluoride etherate (20 ml) was refluxed for 1 hr. After cooling, the reaction mixture was poured into water and the product was extracted with methylene chloride. The organic layer was washed with water and dried over magnesium sulphate. Evaporation of solvent afforded an oil which was chromatographd through a silica gel column (10 g) using 10% acetone in benzene to yield an oil (20.3 mg) of diastereoisomeric mixture of dihydro-3-(1,2,3,4-tetrahydro-1-methylcarbazole)-2(3H)-furanone: nmr(CDCl$_3$) δ 1.35 and 1.75 (singlets, 3H), 2.6–3.1 (m, 3H), 3.9–4.5 (m, 2H), 6.9–7.5 (m, 4H) and 9.95 (broad, 1H); and Anal. Calcd for $C_{17}H_{19}NO_2$: C, 75.81% H, 7.11% N, 5.20% and Found: C, 75.72% H, 7.31% N, 4.94%.

The isomeric mixture of the latter furanone (6.50 g, 0.024 mole) was dissolved in 250 ml of a solution of 45% dimethylamine, the amine of formula HNR$^5$R$^6$ in which $R^5$ and $R^6$ each is methyl, in methanol. The solution was refluxed for 6 days. Evaporation of the solvent afforded an oil (7.40 g) consisting of a mixture of two isomeric amides which was chromatographed through a silica gel column (400 g). Elution with 35% acetone in benzene afforded a residue (3.42 g) which was crystallized from benzene-hexane to give isomer A of 1,2,3,4-tetrahydro-α-(2-hydroxyethyl)-N,N,1-trimethylcarbazole-1-acetamide: mp 168°–169° C.; nmr (CDCl$_3$) δ 1.3 (s, 3H), 3.1 (s, 3H), 3.25 (s, 3H), 7.15 (m, 4H) and 10.7 (s, 1H); and Anal. Calcd for $C_{19}H_{26}N_2O_2$: C, 72.57% H, 8.34% N, 8.91% and Found: C, 72.69% H, 8.35% N, 8.65%. Elution of the latter column with 75% acetone in benzene gave a residue (2.4 g) which was crystallized from dichloromethanehexane to obtain isomer B of 1,2,3,4-tetrahydro-α-(2-hydroxyethyl)-N,N,1-trimethylcarbazole-1-acetamide; mp 145°–146° C.; and nmr(CDCl$_3$) δ 1.45 (s, 3H), 2.5 (s, 3H), 2.75 (s, 3H), 7.2 (m, 4H) and 8.05 (s, 1H).

A solution of isomer A of the latter acetamide (2.91 g, 0.0092 moles) in dry tetrahydrofuran (30 ml) was added dropwise to a stirred suspension of lithium aluminum hydride (0.873 g, 0.023 moles) in dry tetrahydrofuran (30 ml) cooled to 0° C. The mixture was stirred at reflux for one hour. After cooling in ice-water bath, a water-tetrahydrofuran (1:1) mixture was added dropwise to destroy the excess hydride. The inorganic salts were filtered off, and the filtrate was concentrated and dissolved in chloroform. The chloroform layer was washed twice with water, dried over magnesium sulfate and concentrated to yield a residue (2.49 g) which was crystallized out of chloroform and hexane to give 1.75 g of isomer-A of the title compound: mp 249°–251° C.; nmr(CDCl$_3$) δ 1.2 (s, 3H), 1.93 (s, 6H), 3.2 (m, 2H), 5.8 (broad, 1H), 7.0 (m, 4H) and 10.6 (s, 1H); and Anal. Calcd for C$_{19}$H$_{28}$N$_2$O: C, 75.95% H, 9.39% N, 9.33% and Found: C, 75.91% H, 9.39% N, 9.19%.

Similarily, by replacing isomer-A with isomer-B of the above acetamide, isomer-B of the title compound is obtained: mp 214°–215° C. (crystallized from dichloromethane-diethyl ether-hexane); nmr(CDCl$_3$) δ 1.33 (s, 3H), 2.3 (s, 6H), 3.5 (m, 2H), 7.2 (m, 4H) and 8.5 (s, 1H); and Anal. Calcd for C$_{19}$H$_{28}$N$_2$O: C, 75.95% H, 9.39% N, 9.33% and Found: C, 75.80% H, 9.56% N, 9.46%.

By following the procedure of this example and using the appropriate compounds of formulae IV, V and VIII and amine of formula HNR$^5$R$^6$, other compounds of formula I are obtained. For example, by using 3-(2-bromoethyl)-4-chloroindole, ethyl acetoacetate γ-butyrolactone and dimethylamine, 5-chloro-γ-[(dimethylamino)methyl]-1-methyl-1,2,3,4-tetrahydrocarbazole-1-propanol is obtained.

Similarily, by replacing ethyl acetoacetate with an equivalent amount of 3-oxopropanoic acid, ethyl ester or 3-oxopentanoic acid, ethyl ester, the following compounds of formula I are obtained, respectively: γ-[(dimethylamino)methyl]-1,2,3,4-tetrahydrocarbazole-1-propanol and γ-[(dimethylamino)methyl]-1-ethyl-1,2,3,4-tetrahydrocarbazole-1-propanol.

EXAMPLE 2

Alternative Preparation of Dihydro-3-(1,2,3,4-tetrahydro-1-methylcarbazole-2(3H)furanone (II: R$^1$=Me, R$^2$, R$^3$ and R$^4$=H, and m and n=2)

A solution consisting of 1-methyl-2-oxocyclohexane-1-acetic acid methyl ester (18.4 g, 0.1 mole), trimethylorthoformate (13.1 ml, 0.12 mole) and 15 drops of concentrated sulfuric acid, in anhydrous methanol, was refluxed for 4 hours. After cooling, enough 50% sodium hydroxide was added dropwise to dissipate the dark red color to light yellow-orange solution. This solution was evaporated and the residue was partitioned between diethyl ether and 5% aqueous sodium bicarbonate. The ethereal layer was washed with brine and dried over magnesium sulfate. Evaporation of the solvent, gave an oil (19.6 g) which was distilled under reduced pressure through a short vigreux column to yield 15.32 g of 2-methoxy-1-methyl-2-cyclohexane-1-acetic acid, methyl ester; ir(film) 1730 and 1650 cm$^{-1}$; and nmr(CDCl$_3$) δ 1.2 (s, 3H), 1.3–2.2 (m, 6H), 2.45 (s, 2H), 3.45 (s, 3H), 3.65 (s, 3H) and 4.55 (t, 1H).

A solution of diisopropylamine (0.7 ml, 0.005 moles) in anhydrous tetrahydrofuran (10 ml) was coold to about 4° C. and stirred under nitrogen. A 1.82 M solution of butyllithium in hexane (2.75 ml, 0.005 moles) was added slowly (through a septum) at such rate to maintain the temperature at about 4° C. Stirring was continued for 15 minutes at about 4° C. then the solution was cooled to −78° C. To this was added (through a septum) 2-methoxy-1-methyl-2-cyclohexene-1-acetic acid, methyl ester (1.0 g, 0.005 moles) and stirring was continued for 1 hour at −78° C. A mixture of allylbromide (0.52 ml, 0.0055 moles) and hexamethylphosphoric triamide (0.3 ml) was then added to the solution and stirring was continued at −78° C. for 15 minutes. The solution was warmed to −50° C. and stirring was continued for 0.5 hour at this temperature. Then the solution was slowly allowed to reach room temperature and stirring was continued overnight. Hydrochloric acid 2 N (20 ml) was added to the stirred solution which was then poured onto ice water. The product was extracted with diethyl ether, the organic solution was washed with a saturated sodium bicarbonate solution, and dried over magnesium sulfate. Evaporation of the solvent gave 1.19 g of an oil which was chromatographd through a silica gel column (50 g) using 1% acetone in benzene to give an oil (0.50 g) of 2-methoxy-1-methyl-α-(2-propenyl)-2-cyclohexene-1-acetic acid; methyl ester; ir(film) 3050, 1725, 1650 and 1630 cm$^{-1}$; and nmr(CDCl$_3$) δ 1.2 (s, 3H), 1.4–2.4 (m, 9H), 3.4 (s, 3H), 3.55 (s, 3H), 4.55 (t, 1H), 4.95 (m, 2H), and 5.4–5.7 (m, 1H).

To the latter enol ether (4.7 g, 0.020 moles) in methanol (90 ml), was added water (13 ml) and concentrated hydrochloric acid (13 drops). This solution was stirred and refluxed for one hour. After cooling the methanol was evaporated to give an oil which was partitioned between diethyl ether and water. The ethereal phase was washed with saturated sodium bicarbonate solution and water, and dried over magnesium sulfate. Evaporation of the solvent gave a crude product (4.12 g) of 1-methyl-α-(2-propenyl)-2-oxocyclohexane-1-acetic acid, methyl ester; ir(film) 1730, 1710 and 1630 cm$^{-1}$; and nmr(CDCl$_3$) δ 1.10 and 1.15 (singlets, 3H), 2.85–3.1 (m, 1H), 3.57 and 3.65 (singlets, 3H), 4.95 (m, 2H) and 5.4–6.0 (m, 1H).

A mixture of the latter keto ester (36.0 g, 0.161 mole) and phenylhydrazine (16 ml, 0.161 mole) in isobutanol (600 ml) was refluxed under anhydrous conditions for 24 hours. After cooling, the solvent was evaporated to give an oil to which was added a 10% aqueous sulfuric acid solution (600 ml). The resulting mixture was refluxed for 15 minutes with a vigorous mechanical stirring. The cooled mixture was saturated with sodium chloride and the product was extracted with a diethyl ether:dichloromethane (3:1) mixture. The organic layer was washed with a saturated sodium bicarbonate solution and brine, and dried over magnesium sulfate. Evaporation of the solvent gave an orange oil (39.2 g) which was chromatographed through a silica gel column (1.2 kg), using a benzene:petroleum ether (3:1) mixture, to give an oil (5.81 g). This oil was crystallized from petroleum ether to give 1,2,3,4-tetrahydro-α-(2-propenyl)-1-methylcarbazole-1-acetic acid, methyl ester; mp 115°–116° C.; nmr(CDCl$_3$) δ 1.35 (s, 3H), 1.6–2.2 (m, 6H), 2.4–2.9 (m, 3H), 3.80 (s, 3H), 4.95 (m, 2H), 5.4–5.9 (m, 1H), 6.95–7.5 (m, 4H) and 9.6 (broad, 1H); and Anal. Calcd for C$_{19}$H$_{23}$NO$_2$: C, 76.74% H, 7.79%, N, 4.76% and Found: C, 76.49% H, 7.86% N, 4.65%.

Osmium tetroxide (7.50 g, 0.029 mole) in dry tetrahydrofuran (30 ml) was added to a stirred solution at −78° C. of the latter olefinic ester (7.98 g, 0.027 mole) in dry pyridine (30 ml) and dry tetrahyrofuran (75 ml). Stirring was continued at −78° C. for 10 minutes and at 0° C. for 1.5 hours. The reaction mixture was then stirred with a solution of sodium bisulfite (15.0 g) in water (150 ml) and pyridine (150 ml) for 30 minutes at room temperature. The mixture was poured into water (2000 ml) and the product was extracted with ethyl acetate. The organic phase was washed with 2 N hydrochloric acid, saturated sodium bicarbonate solution and water, and dried over magnesium sulfate. Evaporation of the solvent gave an oil (8.86 g) which was chromatographed through a silica gel column (250 g) using 35% acetone in benzene, to give 1,2,3,4-tetrahydro-α-(2,3-dihydroxypropyl)-1-methylcarbazole-1-acetic acid, methyl ester (6.98 g): ir(CHCl₃) 3560, 3380 and 1712 cm⁻¹; and nmr(CDCl₃) δ 1.35 (s, 3H), 3.82 (s, 3H), 7.25 (m, 4H) and 9.55 (broad, 1H).

A stirred solution of the latter diol (296 mg, 0.0009 mole) in acetone:water (1:1) (5 ml) was heated to 65° C. Then was added in one portion a solution of sodium metaperiodate (192 mg, 0.0009 mole), in water (1.5 ml). After 30 seconds, 1 drop of phosphoric acid was added and heating at 65° C. was continued for 25 min. After cooling, the solution was poured into water and the product was extracted with diethyl ether. The ethereal solution was washed with water and dried over magnesium sulfate. Evaporation of the solvent gave an oil (252 mg) which was chromatographed through a silica gel column (30 g) using 10% acetone in benzene to give 1,2,3,3a,4,5,6-heptahydro-1-hydroxy-3a-methyl-10b-azofluoranthene-3-formic acid, methyl ester (0.155 g): ir(CHCl₃) 3550 and 1725 cm⁻¹; and nmr(CDCl₃) δ 1.25 and 1.40 (singlets, 3H), 3.7 (s, 3H), 6.05 (broad, 1H) and 7.0-7.4 (m, 4H).

Sodium borohydride (0.876 g, 0.024 mole) was added to a stirred solution of the latter hydroxy ester (6.84 g, 0.023 mole) in ethanol (135 ml). Stirring was continued at room temperature for 17 hours. The solvent was evaporated and the residue was partitioned between diethyl ether and water. The ethereal phase was washed with water and dried over magnesium sulfate. Evaporation of the solvent gave an oil (5.896 g) which was chromatographed through a silica gel column (300 g) using 5% acetone in benzene to give a diastereoisomeric mixture of the title compound (4.097 g), which is identical to that prepared in Example 1.

EXAMPLE 3

α-(N,N-Dimethylaminomethyl)-1,2,3,4-tetrahydrocyclopent[b]indole-3-propanol (I: $R^1$, $R^2$, $R^3$ and $R^4$=H, $R^4$ and $R^5$=Me, m=2 and n=1)

α-Bromobutyrolactone (33.0 g, 0.2 mole) was added dropwise to a well stirred suspension of a mixture of ethyl and methyl esters of 2-oxycyclopentanecarboxylate (15.06 g, 0.1 mole) and potassium carbonate (55.2 g, 0.4 mole) in dry acetone (150 ml). The mixture was refluxed for 4.5 hours and became deep purple. The mixture was filtered and the filtrate was evaporated to dryness. The residue was partitioned between water and diethyl ether. The organic phase was washed with brine, dried over magnesium sulfate and concentrated. The residue (28.4 g) was distilled under vacuum to afford a mixture (16.5 g) of the methyl and ethyl esters of 1-(2-oxotetrahydrofuran-3-yl)-2-oxocyclopentanecarboxylic acid: nmr(CDCl₃) δ 1.3 (t, 60% of 3H), 1.6-3.0 (m, 8H), 3.4 (m, 1H), 3.75 (m, 40% of 3H) and 3.9-4.5 (m, 4H).

A suspension of the latter mixture (36.1 g, 0.15 mole) in 20% aqueous sulfuric acid (175 ml) was heated with stirring on steam bath overnight. A clear homogeneous solution was obtained. After cooling to room temperature, it was saturated with salt and extracted with ethyl acetate. The organic extracts were combined and washed with brine, dried over magnesium sulfate, filtered and concentrated in a regular distillation apparatus. The residue was distilled at 125°-7° C. under 0.3 mm Hg using a Vigreux distilling unit to yield 17.1 g of 4,5-dihydro-3-(2-oxocyclopentan-1-yl)-2(3H)-furanone: bp 125°-127° C./0.3 mm Hg; nmr(CDCl₃) δ 1.6-3.3 (m, 10H) and 4.3 (m, 2H); and Anal. Calcd for C₉H₁₂O₃: C, 64.27% H, 7.19% and Found: C, 63.56% H, 7.22%.

A mixture of the latter compound (19.4 g, 0.080 mole) and phenylhydrazine hydrochloride (12.71 g, 0.088 mole) in acetic acid (100 ml) was refluxed for 55 min, cooled and poured slowly over ice-water (500 ml). The cooled solution was basified with sodium carbonate and extracted with chloroform. The organic layer was washed with brine, dried over magnesium sulfate and concentrated to give 25.1 g of brown oil which was chromatographed on silica gel (750 g) with 7.5% acetone-benzene mixture. The initial fractions were collected (4.89 g) and crystallized from benzene-hexane to give dihydro-3-(1,2,3,4-tetrahydrocyclopent[b]indol-3-yl)-2(3H)-furanone: mp 155°-157° C.; nmr(CDCl₃) δ 2.5 (m, 8H), 4.2 (m, 2H), 7.25 (M, 4H) and 9.3 (broad, 1H); and Anal. Calcd for C₁₅H₁₅NO₂: C, 74.66% H, 6.27% N, 5.81% and Found: C, 74.77% H, 6.36% N, 6.07%.

A suspension of the latter compound (3.2 g, 0.013 mole) in methanol (200 ml) was treated with dimethylamine gas (25 ml) and refluxed with stirring for 72 hr. Methanol was distilled off and the residue was chromatographed on silica gel (140 g) with 10% acetone-benzene. The initial less polar fractions were collected and crystallized from benzene-hexane to give 1.74 g of isomer A of α-(2-hydroxyethyl)-N,N-dimethyl-1,2,3,4-tetrahydrocyclopent[b]indole-3-acetamide; mp 118°-120° C.; nmr(CDCl₃) δ 1.7 (m, 2H), 2.2 (m, 1H), 2.8 (m, 4H), 2.95 (s, 3H), 3.06 l (s, 3H), 3.5 (m, 4H), 7.15 (m, 4H) and 9.0 (s, 1H); and Anal. Calcd for C₁₇H₂₂N₂O₂: C, 71.30% H, 7.74% N, 9.78% and Found: C, 71.12% H, 7.74% N, 9.64%. The latter more polar fractions were collected and crystallized from benzene-hexane to give 1.06 g of isomer B of α-(2-hydroxyethyl)-N,N-dimethyl-1,2,3,4-tetrahydrocyclopent[b]indole-acetamide; mp 135°-137° C.; nmr(CDCl₃) δ 2.72 (s, 3H), 2.92 (s, 3H), 7.15 (m, 4H), and 8.3 (s, 1H); and Anal. Found: C, 71.49% H, 7.81% N, 9.69%.

A solution of isomer A of α-(2-hydroxyethyl)-N,N-dimethyl-1,2,3,4-tetrahydrocyclopent[b]indole-3-acetamide (1.72 g, 0.0060 mole) in dry tetrahydrofuran (50 ml) was added dropwise to a stirred suspension of lithium aluminium hydride (0.68 g, 0.018 mole) in dry tetrahydrofuran (50 ml) at 0° C. under nitrogen. The suspension was stirred and refluxed for three hr. It was cooled in an ice-bath and a mixture of water-tetrahydrofuran (1:4) was added carefully to destroy excess lithium aluminium hydride. The inorganic salts were filtered through a celite pad and the filtrate was diluted with diethyl ether, washed with brine, dried over magnesium sulfate and concentrated to afford an off-white solid (1.53 g). It was recrystallized from dichloromethane-benzene-hexane to give 0.90 g of isomer A of the title compound: mp 152°-153° C.; nmr(CDCl₃) δ 2.2 (s, 6H), 3.7 (m, 2H), 7.15 (m, 4H) and 8.4 (s, 1H) and Anal. Calcd for C₁₇H₂₄N₂O: C, 74.96% H, 8.83% N, 10.29% and Found: C, 75.09% H, 9.09% N, 10.39%.

The latter reduction was repeated using isomer of B of α-(2-hydroxyethyl)-N,N-dimethyl-1,2,3,4-tetrahydrocyclopent[b]indole-acetamide to give isomer B of the title compound: mp 168°-169° C.; nmr(CDCl₃) δ 2.22 l (s, 6H), 7.2 (m, 4H), 7.25 (s, 1H) and 8.8 (s, 1H); and Anal. Calcd for C₁₇H₂₄N₂O: C, 74.96% H, 8.88% N, 10.29% and Found: C, 74.96% H, 9.18% N, 10.01%.

We claim:
1. A compound of formula III

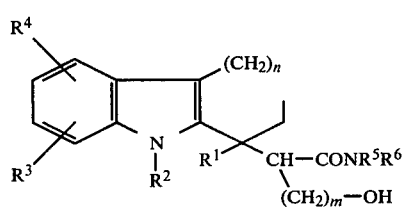
(III)
in which $R^1$ and $R^2$ each is hydrogen or lower alkyl; $R^3$ and $R^4$ each is hydrogen, lower alkyl, halo, nitro, trifluoromethyl or lower alkoxy; $R^5$ and $R^6$ each is hydrogen or lower alkyl or $R^5$ and $R^6$ together with the nitrogen atom to which they are attached form a pyrrol-1-yl, piperidin-1-yl or morpholin-4-yl; m is 2 or 3; and n is 1 or 2.
* * * * *